United States Patent
Gurjar et al.

(10) Patent No.: US 9,006,453 B2
(45) Date of Patent: Apr. 14, 2015

(54) PROCESS FOR PREPARATION OF ZOLMITRIPTAN

(75) Inventors: Mukund Keshav Gurjar, Pune (IN);
Neelakandan Kaliaperumal, Pune (IN);
Pravin Prabhakar Ahirrao, Pune (IN);
Raghuramireddy Baireddy, Pune (IN);
Prabhakaran Balasubramanian, Pune (IN); Srinivas Nandala, Pune (IN);
Prasad Pandurang Panchabhai, Pune (IN); Samit Satish Mehta, Pune (IN)

(73) Assignee: Emcure Pharmaceuticals Limited (IN)

( * ) Notice: Subject to any disclaimer, the term of this patent is extended or adjusted under 35 U.S.C. 154(b) by 0 days.

(21) Appl. No.: 14/342,368

(22) PCT Filed: Aug. 27, 2012

(86) PCT No.: PCT/IN2012/000568
§ 371 (c)(1),
(2), (4) Date: Feb. 28, 2014

(87) PCT Pub. No.: WO2013/057739
PCT Pub. Date: Apr. 25, 2013

(65) Prior Publication Data

US 2014/0228582 A1 Aug. 14, 2014

(30) Foreign Application Priority Data

Sep. 2, 2011 (IN) .......................... 2452/MUM/2011

(51) Int. Cl.
*C07D 413/06* (2006.01)
*C07D 263/20* (2006.01)

(52) U.S. Cl.
CPC ............ *C07D 413/06* (2013.01); *C07D 263/20* (2013.01)

(58) Field of Classification Search
CPC ... C07D 263/20; C07D 263/22; C07D 413/06
USPC ......................................................... 548/229
See application file for complete search history.

(56) References Cited

U.S. PATENT DOCUMENTS 5,466,699 A    11/1995  Robertson et al.

FOREIGN PATENT DOCUMENTS

| WO | 97/06162 | 2/1997 |
| WO | 2008/018090 | 2/2008 |
| WO | 2009/044211 | 4/2009 |

OTHER PUBLICATIONS

Kihwan Moon, International Preliminary Report on Patentability in PCT/IN2012/000568, Mar. 4, 2014, 7 pages, The International Bureau of WIPO, Geneva, Switzerland.
Wang Ji, International Search Report in PCT/IN2012/000568, May 2, 2013, 5 pages, The State Intellectual Property Office, the P.R. China, Beijing, China.
Wang Ji, Written Opinion of the International Searching Authority in PCT/IN2012/000568, Apr. 23, 2013, 6 pages, The State Intellectual Property Office, the P.R. China, Beijing, China.

*Primary Examiner* — Joseph Kosack
*Assistant Examiner* — Amanda L Aguirre
(74) *Attorney, Agent, or Firm* — Florek & Endres PLLC

(57) ABSTRACT

The present invention provides a convenient and industrially viable process for preparation of Zolmitriptan (I) having desired purity. The invention specifically relates to a method for isolating (S)-4-(4-hydrazinobenzyl)-1,3-oxazolidin-2-one hydrochloride (IIIa) of desired purity by separating the undesired inorganic side products such as stannous hydroxide by manipulation of pH at different stages and finally treating with N,N-dimethylamino butyraldehyde diethyl acetal in an acidic medium to provide Zolmitriptan (I) conforming to regulatory specifications.

16 Claims, No Drawings

PROCESS FOR PREPARATION OF ZOLMITRIPTAN

This application is a U.S. National Stage filing under 35 U.S.C. §371 of International Application No. PCT/IN2012/000568, filed Aug. 27, 2012, which in turn claims priority to Indian Patent Application No. 2452/MUM/2011, filed Sep. 2, 2011.

FIELD OF THE INVENTION

The present invention relates to a novel and cost-effective process for the preparation of Zolmitriptan. The invention specifically relates to the preparation and isolation of a key intermediate, (S)-4-(4-hydrazinobenzyl)-1,3-oxazolidin-2-one hydrochloride of formula (III) starting from (S)-4-(4-aminobenzyl)-1,3-oxazolidin-2-one of formula (II) which helps in obtaining Zolmitriptan of desired purity.

BACKGROUND OF THE INVENTION

Zolmitriptan (I) chemically known as (4S)-4-[[3-2-(dimethylamino)ethyl]-1H-indol-5-yl]methyl]-2-oxazolidinone, belongs to the triptan family of compounds and is a selective serotonin receptor agonist of the 1B and 1D subtypes. It is used in the acute treatment of migraine attacks with or without aura and also in cluster headaches. Zolmitriptan is available under various brand names such as Zomig, Zomigon, AscoTop, Zomigoro, Flezol etc.

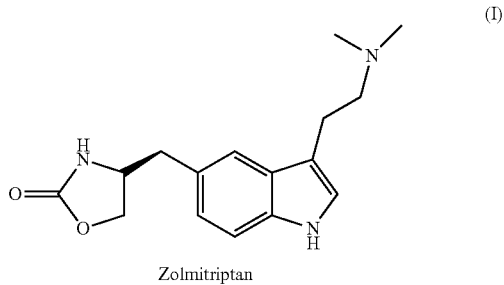

Zolmitriptan

Zolmitriptan was first disclosed in U.S. Pat. No. 5,466,699 and the synthetic route comprises diazotization of (S)-4-(4-aminobenzyl)-1,3-oxazolidin-2-one with sodium nitrite in presence of hydrochloric acid, followed by treatment of the diazonium salt with stannous chloride to give (S)-4-(4-hydrazinobenzyl)-1,3-oxazolidin-2-one. Further reaction of the hydrazine derivative with dimethylamino butyraldehyde diethyl acetal followed by chromatographic purification gave Zolmitriptan (I) as oil, which upon further crystallization from isopropanol gave Zolmitriptan of desired purity. (S)-4-(4-aminobenzyl)-1,3-oxazolidin-2-one, in turn, was obtained from L-4-nitrophenyl alanine by treating it with thionyl chloride and methanol to give (S)-methyl-4-nitrophenyl alanate, which on reduction with sodium borohydride gave the corresponding alcohol. Further reaction of the said alcohol with phosgene in presence of potassium hydroxide followed by hydrogenation in presence of palladium on carbon gave the desired (S)-4-(4-aminobenzyl)-1,3-oxazolidin-2-one.

A significant disadvantage of this method involves the utilization of a relatively large excess of stannous chloride, in the range of about 4.7 molar equivalents during the preparation of the intermediate, (S)-4-(4-hydrazinobenzyl)-1,3-oxazolidin-2-one hydrochloride, which results in formation of large amounts of stannous hydroxide. Also, the hydrazine intermediate thus obtained requires a highly energy intensive procedure of distilling out large volumes of aqueous mass followed by trituration with a low boiling and flammable solvent like ether. The utilization of excess stannous chloride generates high level of associated impurities in the intermediate due to which repeated purification involving column chromatography is required for obtaining the desired purity of Zolmitriptan. Successive purification results in a low yield of about (18% w/w) hence, the method is not preferred for commercial scale.

WO 97/06162 discloses a one-pot process for the conversion of (S)-4-(4-aminobenzyl)-1,3-oxazolidin-2-one to Zolmitriptan (I) wherein the amine derivative is diazotized using sodium nitrite and the resulting diazonium salt is reduced using sodium sulfite to give the corresponding hydrazine derivative, which then requires an abnormally high volume of solvent during reaction with 4,4-diethoxy-N,N-dimethylbutylamine to yield Zolmitriptan.

The process, despite avoiding the use of stannous chloride and isolation of intermediates, resorts to large amounts of sodium sulfite as reducing agent and due to the in-situ mode of reactions, the associated impurities which are generated in significant proportions are carried forward thereby necessitating laborious purification methods to obtain Zolmitriptan with reduced yield.

WO2009/044211 discloses a process for synthesis of Zolmitriptan wherein (S)-4-(4-aminobenzyl)-1,3-oxazolidin-2-one is diazotized using sodium nitrite, followed by reduction of the diazonium salt to the corresponding hydrazine derivative using stannous chloride. Further reaction of the hydrazine derivative with 4,4-diethoxy-N,N-dimethylbutylamine and cyclization gave Zolmitriptan. The specification also discloses a one-pot synthesis method wherein very high dilutions are necessary to minimize the formation of associated impurities generated during the reaction. Due to the in-situ nature of the method, the undesirable side products in the penultimate step is carried forward to yield an impure product, and necessitates a number of purification steps to obtain the final product having desired purity.

Thus, there is a need for a process wherein the associated impurities are minimized and removed during isolation of intermediates without an additional step of purification and wherein such a procedure does not involve energy intensive and time consuming unit processes such as solvent distillation for obtaining either the intermediates or the final product. Therefore, the present inventors in their quest for developing a method which provides intermediates which are substantially free from associated impurities and results in a high-yielding, scalable chemical process for the synthesis of Zolmitriptan (I), have, after rigorous experimentation, developed a method which provides a method for isolation of (S)-4-(4-hydrazinobenzyl)-1,3-oxazolidin-2-one hydrochloride of formula (IIIa) by overcoming the shortcomings of the prior art and helps in providing Zolmitriptan of desired purity.

OBJECT OF THE INVENTION

An objective of the present invention is to provide a convenient and cost-effective process for preparation of Zolmitriptan (I) conforming to regulatory specifications wherein (S)-4-(4-hydrazinobenzyl)-1,3-oxazolidin-2-one hydrochloride of formula (IIIa) having desired purity is obtained.

Yet another object of the invention is to obtain (S)-4-(4-hydrazinobenzyl)-1,3-oxazolidin-2-one hydrochloride of formula (IIIa) having desired purity by employing an isolation method which involves separation of undesired side products and impurities formed during the reaction by careful manipulation of pH at various stages.

SUMMARY OF THE INVENTION

The present invention relates to a novel process for synthesis of Zolmitriptan (I) comprising separation of associated impurities during the isolation of (S)-4-(4-hydrazinobenzyl)-1,3-oxazolidin-2-one hydrochloride, which helps in obtaining Zolmitriptan (I) conforming to regulatory specifications.

An aspect of the present invention relates to an improved process for the preparation of Zolmitriptan (I), comprising
a) reaction of an aqueous solution of diazotized (S)-4-(4-aminobenzyl)-1,3-oxazolidin-2-one with stannous chloride in hydrochloric acid at −15 to 10° C., adjusting pH of the reaction mixture between 2 to 6 after completion of reaction, filtering and readjusting the pH of the filtrate between 6 and 10 to obtain (S)-4-(4-hydrazinobenzyl)-1,3-oxazolidin-2-one of formula (III), which was then converted to (S)-4-(4-hydrazinobenzyl)-1,3-oxazolidin-2-one hydrochloride of formula (IIIa) by treatment with hydrochloric acid in isopropanol,
b) treating (S)-4-(4-hydrazinobenzyl)-1,3-oxazolidin-2-one hydrochloride of formula (IIIa) with N,N dimethylamino butyraldehyde diethyl acetal (IV) in aqueous medium at ambient to reflux temperature, cooling the mixture, adjusting the pH of the reaction mixture between 7 to 8 and isolating Zolmitriptan (I) of desired purity.

The objectives of the present invention will be apparent from the following detailed description

DETAILED DESCRIPTION OF THE INVENTION

It was observed by the present inventors that during the reduction of diazonium salt obtained by diazotization of (S)-4-(4-aminobenzyl)-1,3-oxazolidin-2-one (II) with stannous chloride, side products such as stannous hydroxide were separating out along with (S)-4-(4-hydrazinobenzyl)-1,3-oxazolidin-2-one of formula (III) and were interfering with its isolation to give a slimy product. Hence, prior art methods invariably required in-situ treatment of the compound (III) with N,N-dimethylamino butyraldehyde diethyl acetal (IV).

During the in-situ reaction, it was found that since the exact amount of compound (III) formed was not known, therefore, there used to be excess addition of the compound (IV) for reaction with (S)-4-(4-hydrazinobenzyl)-1,3-oxazolidin-2-one of formula (III). The excess compound of formula (IV) which was added was also found to be decomposed by stannic chloride which was formed from stannous hydroxide during the reaction in presence of HCl.

Due to the above difficulties, prior art methods did not yield the compound of formula (III) and subsequently Zolmitriptan (I) of the desired purity. The product and the intermediate thus obtained required successive purifications, which increased the production costs exorbitantly.

In an effort to minimize the interference of inorganic side products, prior art processes resorted to methods such as dilution with water. However, addition of water decreased the batch size, substantially increased energy loads and was found to be cost prohibitive.

In view of the above difficulties, the present inventors carried out rigorous experimentation to overcome these problems, and quite unexpectedly, it was found that during work up and isolation of the compound of formula (III), stannous hydroxide and other associated impurities formed during the reaction could be separated from the reaction mass by manipulating the pH of the reaction medium at various stages.

At a particular pH range, the side products, stannous hydroxide being major amongst them, was almost completely separated, due to which, the intermediate, (S)-4-(4-hydrazinobenzyl)-1,3-oxazolidin-2-one of formula (III) of desired purity could be isolated. This helped in lowering the consumption of N,N-dimethylamino butyraldehyde diethyl acetal (IV) in the final step to give Zolmitriptan (I) of high purity having impurity levels conforming to regulatory specifications.

Scheme 1: Method embodied in the present invention for the preparation of Zolmitriptan (I)

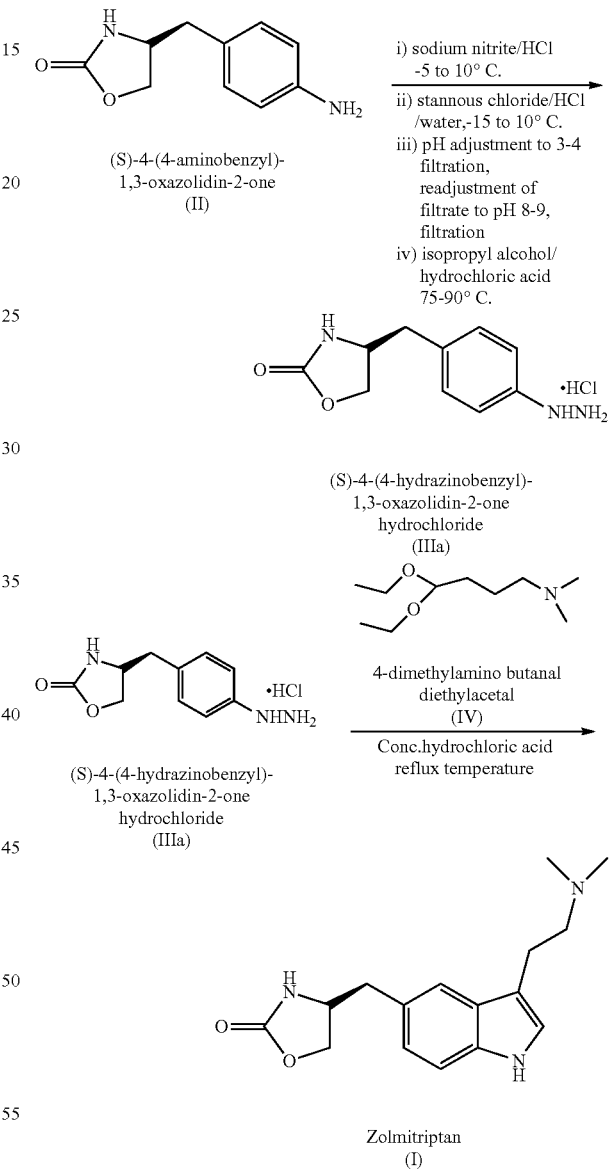

In an embodiment, (S)-4-(4-aminobenzyl)-1,3-oxazolidin-2-one of formula (II), which was prepared using prior art methods was treated with an aqueous solution of sodium nitrite in concentrated hydrochloric acid at −5 to 10° C. After completion of reaction based on HPLC, the resulting diazonium salt was treated with stannous chloride in hydrochloric acid at −15 to 10° C. to give (S)-4-(4-hydrazinobenzyl)-1,3-oxazolidin-2-one of formula (III).

After completion of the reaction based on HPLC, the pH of the reaction mass was adjusted in the range of 2.0 to 6.0 using aqueous sodium hydroxide solution. The resulting reaction mixture was stirred, cooled and filtered to separate the impurities. The filtrate was optionally washed with an organic solvent such as dichloromethane and further treated with aqueous sodium hydroxide solution till a pH range of 6.0 to 10.0 was attained. The reaction mass was stirred, cooled and filtered to give (S)-4-(4-hydrazinobenzyl)-1,3-oxazolidin-2-one (III) of desired purity.

It is pertinent to note that the inventors have been able to separate the undesired side product and the key intermediate from the reaction mass by employing a simple but effective technique of controlling the pH of reaction mixture. On the other hand, prior art methods accomplish separation of the intermediate from the reaction mixture by energy intensive techniques such as distillation of water from the reaction mass followed by trituration with solvent ether.

Compound (III) was treated with hydrogen chloride in an alcohol in the temperature range of 75 to 90° C., followed by cooling and filtration to obtain (S)-4-(4-hydrazinobenzyl)-1,3-oxazolidin-2-one hydrochloride of formula (IIIa). The alcohol was selected from the group comprising methanol, ethanol, n-butanol, isobutanol, n-propanol, isopropanol etc Compound (IIIa) was then treated with N,N dimethylamino butyraldehyde dimethyl acetal or N,N-dimethylamino butyraldehyde diethyl acetal in presence of concentrated hydrochloric acid in aqueous medium. The reaction was carried out at ambient to reflux temperature and upon completion of the reaction, the pH of the reaction mass was adjusted between 7.0 and 8.0 with a base selected from the group comprising of sodium carbonate, sodium bicarbonate, sodium acetate, aqueous ammonia, potassium carbonate and potassium bicarbonate.

The reaction mass was then washed with an alkyl acetate like ethyl acetate and was made alkaline in the range of 8.0 to 12.0 with an inorganic base and extracted with a chlorinated organic solvent.

The chlorinated organic solvent was selected from the group comprising of chloroform, dichloromethane, ethylene dichloride etc., but preferably dichloromethane.

The organic layer was concentrated to provide a residue, which was diluted with ethyl acetate, cooled and filtered to give Zolmitriptan (I) having purity conforming to regulatory specifications.

The following examples are meant to be illustrative of the present invention. These examples exemplify the invention and are not to be construed as limiting the scope of the invention.

EXAMPLES

Example 1

Synthesis of (S)-4-(4-hydrazinobenzyl)-1,3-oxazolidin-2-one hydrochloride (IIIa)

A mixture of (S)-4-(4-aminobenzyl)-1,3-oxazolidin-2-one (100 gms) and concentrated hydrochloric acid (250 ml) in water (500 ml) was treated with an 50% aqueous solution of sodium nitrite (46 gms) at −5 to 10° C. Upon completion of the reaction, as monitored by TLC, the reaction mass was further treated with stannous chloride dihydrate (420 gms) dissolved in concentrated hydrochloric acid (500 ml) and water (544 ml) at −15 to 10° C. When the reaction was complete, as monitored by HPLC, the pH of the reaction mass was adjusted in the range of 2.0 to 6.0 by adding aqueous sodium hydroxide solution. The reaction mass was cooled and filtered to separate the solid. The aqueous layer was extracted with dichloromethane and further made alkaline in the pH range of 6.0 to 10.0 with aqueous sodium hydroxide. The mixture was cooled and filtered to give solid (S)-4-(4-hydrazinobenzyl)-1,3-oxazolidin-2-one (III), which was then suspended in isopropanol (420 ml) and converted to the hydrochloride salt by treatment with hydrogen chloride at reflux temperature to yield the hydrochloride salt of (S)-4-(4-hydrazinobenzyl)-1,3-oxazolidin-2-one (IIIa).
Yield: 85 g
Purity (HPLC)≈99%

Example 2

Synthesis of Zolmitriptan (I)

Example 2

Synthesis of Zolmitriptan (I)

Conc. hydrochloric acid (200 ml) was added to (S)-4-(4-hydrazinobenzyl)-1,3-oxazolidin-2-one hydrochloride (100 gms) in water (650 ml) and treated with N,N-dimethylamino butyraldehyde diethyl acetal (95 gms). The reaction mixture was warmed and upon completion of the reaction, as monitored by HPLC; the pH was adjusted in the range of 7.0 to 8.0 using aq. ammonia followed by extraction with ethyl acetate. The organic layer was separated and aqueous layer was made alkaline between pH 8.0 to 12.0 using aq. ammonia and extracted with dichloromethane (750 ml). The organic layer was separated and concentrated to give a residue which was diluted with ethyl acetate (200 ml). The organic layer was concentrated, cooled and filtered to yield pure Zolmitriptan (I).
Yield: 62 gms
Purity (HPLC)≈99.7%

We claim:
1. An improved process for the preparation of Zolmitriptan (I), comprising
   a) reacting an aqueous solution of diazotized (S)-4-(4-aminobenzyl)-1,3-oxazolidin-2-one with stannous chloride in hydrochloric acid at −15 to 10° C.,
   b) adjusting pH of the reaction mass to between 2 to 6 after completion of reaction,
   c) filtering the reaction mass,
   d) readjusting the pH of the filtrate between 6 to 10 to obtain (S)-4-(4-hydrazinobenzyl)-1,3-oxazolidin-2-one of formula (III),
   e) converting (S)-4-(4-hydrazinobenzyl)-1,3-oxazolidin-2-one of formula (III) to (S)-4-(4-hydrazinobenzyl)-1,3-oxazolidin-2-one hydrochloride of formula (IIIa) by treatment with hydrochloric acid in an organic solvent,
   f) treating (S)-4-(4-hydrazinobenzyl)-1,3-oxazolidin-2-one hydrochloride of formula (IIIa) with N,N dimethylaminobutyraldehyde diethyl acetal (IV) in aqueous medium at ambient to reflux temperature,
   g) adjusting the pH of the second reaction mass to between 7 to 8, and
   h) isolating Zolmitriptan (I).

2. The process as claimed in claim 1, wherein the pH of the reaction mass is adjusted to 3-4 in step b).

3. The process as claimed in claim 1, wherein the pH of the filtrate in step d) is readjusted to between 8-9 to obtain (S)-4-(4-hydrazinobenzyl)-1,3-oxazolidin-2-one of formula (III).

4. The process as claimed in claim 1, wherein the organic solvent is an alcohol selected from the group consisting of methanol, ethanol, n-butanol, isobutanol, n-propanol, isopropanol and combinations thereof.

5. The process as claimed in claim 1, further comprising the steps of:
   i. washing the reaction mass obtained in step f) with alkyl acetate,
   ii. readjusting the pH of the washed reaction mass to between 8 to 12,
   iii. extracting the reaction mass with a second organic solvent, and
   iv. concentrating the extract and diluting the residue with ethyl acetate.

6. The process as claims in claim 5, wherein the second organic solvent is a chlorinated solvent.

7. The process according to claim 1, wherein the (S)-4-(4-hydrazinobenzyl)-1,3-oxazolidin-2-one hydrochloride of formula (IIIa) in step e) has a purity of at least 99%.

8. The process according to claim 1, wherein the Zolmitriptan (I) in step h) has a purity of at least 99.7%.

9. The process according to claim 1, wherein the organic solvent comprises isopropanol.

10. The process according to claim 1, wherein the organic solvent consists essentially of isopropanol.

11. The process according to claim 6, wherein the chlorinated solvent is selected from the group consisting of chloroform, dichloromethane, ethylene dichloride and mixtures thereof.

12. The process according to claim 6, wherein the chlorinated solvent comprises dichloromethane.

13. The process according to claim 6, wherein the chlorinated solvent consists essentially of dichloromethane.

14. The process according to claim 1, wherein the treatment with hydrochloric acid in an organic solvent of step e) occurs at a temperature of 75-90° C.

15. The process according to claim 1, wherein the second reaction mass of step g) is adjusted to a pH of 7 to 8 with a base selected from the group consisting of sodium carbonate, sodium bicarbonate, sodium acetate, aqueous ammonia, potassium carbonate, potassium bicarbonate and mixtures thereof.

16. The process according to claim 15, wherein the base comprises aqueous ammonia.

* * * * *